United States Patent [19]
Pickett et al.

[11] Patent Number: 6,143,918
[45] Date of Patent: Nov. 7, 2000

[54] COMPOUNDS BASED ON DIBENZOYLRESORCINOL AND RELATED COMPOSITIONS AND ARTICLES

[75] Inventors: James Edward Pickett, Schenectady; Wen P Liao, Clifton Park; Amy Kathleen Simonian, Clifton Park; Gregory Ronald Gillette, Clifton Park, all of N.Y.

[73] Assignee: General Electric Company, Schenectady, N.Y.

[21] Appl. No.: 09/346,671

[22] Filed: Jul. 2, 1999

Related U.S. Application Data

[62] Division of application No. 08/786,358, Jan. 16, 1997, Pat. No. 5,981,073.

[51] Int. Cl.$^7$ .......................... C07C 69/76; C07C 41/00
[52] U.S. Cl. ............................ 560/52; 548/252; 568/633
[58] Field of Search ............................ 560/52; 568/633; 548/242

[56] References Cited

U.S. PATENT DOCUMENTS

| | | |
|---|---|---|
| 2,794,052 | 5/1957 | Gordon et al. . |
| 2,861,976 | 11/1958 | Gordon et al. . |
| 3,395,184 | 7/1968 | Dressler et al. . |
| 5,391,795 | 2/1995 | Pickett . |

FOREIGN PATENT DOCUMENTS

| | | |
|---|---|---|
| 0672732 | 9/1995 | European Pat. Off. . |
| 0812880 | 12/1997 | European Pat. Off. . |
| 846673 | 6/1998 | European Pat. Off. . |
| 1150178 | 1/1958 | France . |

OTHER PUBLICATIONS

Abstract: "Benzene Derivatives"—Substituted diacylresorcinols. D.A. Gordon (to Dow Chem. Co., Apr. 19, 1960. p. 14190.

Abstract: "Noncondensed Aromatics"—20116z—Methylenebis (benzophenone) derivatives. Minagawa, Motonobu, Kubota, Naohiro, Shibata, Toshihiro (Adeka Argus Chem. Col., Ltd) Japan, vol. 91, 1979.

*Primary Examiner*—Paul J. Killos
*Attorney, Agent, or Firm*—S. Bruce Brown; Noreen C. Johnson

[57] ABSTRACT

Methods for preparing novel dibenzoylresorcinol-based compounds are disclosed, wherein the dibenzoylresorcinol is bonded to the residue of either an alcohol or a carboxylic acid group, via a methylene carboxylate linking group; and wherein the dibenzoylresorcinol is bonded directly to a substituted or unsubstituted aryl group which does not include a pendent hydroxyl group. The groups attached to the dibenzoylresorcinol may contain a wide variety of functional sites which permit further reaction, e.g., copolymerization. The described compounds are very useful as UV light absorbers and may be used to form improved coating compositions which usually include a transparent, polymeric matrix material. The coating compositions may be applied to various substrates, e.g., thermoplastics, to afford a selection of enhanced properties, such as UV light resistance and abrasion resistance.

8 Claims, No Drawings

COMPOUNDS BASED ON DIBENZOYLRESORCINOL AND RELATED COMPOSITIONS AND ARTICLES

This application is a division of application Ser. No. 08/786,358, filed Jan. 16, 1997, now U.S. Pat. No. 5,981,073, which is hereby incorporated by reference in its entirety.

This application is related to U.S. application Ser. No. 08/669,899 filed Jun. 21, 1996 now U.S. Pat. No. 5,869,185 and U.S. application Ser. No. 08/762,644 filed Dec. 9, 1996 now U.S. Pat. No. 5,763,674.

TECHNICAL FIELD

This invention relates generally to chemical technology, and more particularly, to chemical compounds and compositions based on dibenzoylresorcinol.

BACKGROUND OF THE INVENTION

Thermoplastic resins often possess an attractive set of mechanical and physical properties, such as high heat resistance, impact resistance, dimensional stability, high ductility, and optical clarity. Polycarbonates are a good illustration of materials exhibiting many of these attributes. While these properties serve to encourage the use of thermoplastics in many commercial applications, other, less favorable properties often need to be rectified or somehow addressed. As an example, thermoplastics often exhibit low resistance to abrasion and chemical solvents. Moreover, thermoplastic materials are usually susceptible to photodegradation by ultraviolet (UV) light. This type of degradation typically leads to erosion and yellowing of the polymer surface. The discoloration represents a large problem in using products like those based on polycarbonate, which are especially noted for their transparency.

Efforts to alleviate these problems have been undertaken in the past. As an example, coating compositions that include ultraviolet light absorbers have been applied onto thermoplastic substrates and then cured. For the case of polycarbonates, the coating material is often based on a silicone hardcoat matrix, which when cured, provides a good abrasion barrier. The UV absorbing agents incorporated into the hardcoat matrix are often based on benzophenone or benzotriazoles. As described in U.S. Pat. No. 5,391,795 (J. Pickett), various patents disclose this general type of strategy for protecting thermoplastics. For example, U.S. Pat. No. 4,373,061 describes the use of a silicone hardcoat composition comprising benzophenones as the UV absorbing agents, while U.S. Pat. No. 4,278,804 discloses a matrix composition based in part on silanol-reactive alkoxysilyl- or alkanoyloxysilylalkyl ether adducts of aromatic UV absorbing agents. U.S. Pat. No. 5,391,795 itself describes the use of silylated derivatives of 4,6-dibenzoylresorcinols as UV absorbers for hardcoat compositions.

The UV absorbing agents themselves sometimes decompose to some degree, upon exposure to UV light. The decomposition can in turn lead to microcracks in the hardcoat, exposing the underlying polymer surface to the degrading effects of UV light, abrasion, and the like. Thus, the purpose of the hardcoat in protecting the thermoplastic substrate is defeated to some extent.

It's quite apparent that there is a continuing need for new compounds which are effective in providing UV protection for thermoplastics. The compounds should themselves exhibit a high degree of UV stability, i.e., photostability, while still being effective in protecting the substrate. Moreover, the new compounds should be amenable to various forms of use, e.g., they should be capable of being incorporated into a hardcoat composition which is coated onto the surface being protected. The new UV absorbing compounds should also be physically and chemically compatible with the substrate material, and with any type of hardcoat composition being employed. They should not interfere with any of the other properties possessed by the thermoplastic substrate, such as transparency. Furthermore, the new compounds should be relatively easy to manufacture, and their use should not involve an excessive increase in the cost of the thermoplastic product.

SUMMARY OF THE INVENTION

The present invention satisfies substantially all of the needs discussed above. One embodiment is directed to a dibenzoylresorcinol-based compound having the general formula (I):

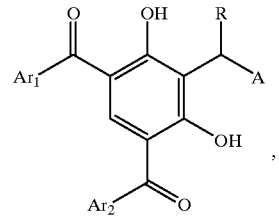

wherein $Ar_1$ and $Ar_2$ are independently substituted or unsubstituted monocyclic or polycyclic aryl groups; and R is hydrogen, an aryl group, or a linear or branched alkyl chain having less than about 10 carbon atoms. The group designated as "A" can be a radical derived from a very wide variety of alcohols or carboxylic acids. In that instance, the compound can be made in a process which usually involves two steps, in which a methylene carboxylate intermediate of 4,6-dibenzoylresorcinol is first prepared, and then reacted with an alcohol or a carboxylic acid to form the desired product. The product can include functional sites which permit further reaction with other materials.

"A" can alternatively be a substituted or unsubstituted aryl group which does not include a pendent hydroxyl group. Various types of aryl groups may be present, such as phenyl, alkyl-substituted phenyl groups, halogen-substituted phenyl groups, and alkoxy-substituted phenyl groups. The desired compounds of this type are prepared in a reaction which usually includes one primary step, involving the reaction of 4,6-dibenzoylresorcinol with a benzyl halide compound, an aqueous base, and a compatible phase transfer catalyst. Again, the product can include functional sites suitable for further reaction.

Another embodiment of this invention is directed to improved coating compositions for protecting thermoplastic substrates. Much of the improvement is a result of the enhanced photostability of the dibenzoylresorcinol compounds briefly described above. The coating compositions include those compounds, incorporated into a matrix composition which may be formed from a variety of materials, such as acrylics.

The protection afforded to the substrates usually relates to ultraviolet light resistance, and can also include other enhancements, such as abrasion resistance. Thus, another embodiment of this invention is directed to improved articles which comprise a substrate (usually thermoplastic), coated with a protective composition which comprises the dibenzoylresorcinol-based compounds described above, incorporated into a matrix composition.

DETAILED DESCRIPTION OF THE INVENTION

As briefly mentioned previously, the compounds of the present invention have the formula

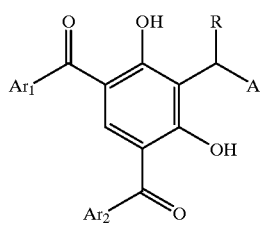

I wherein $Ar_1$ and $Ar_2$ are independently substituted or unsubstituted monocyclic or polycyclic aryl groups; and R is hydrogen, an aryl group, or a linear or branched alkyl chain having less than about 10 carbon atoms. In preferred embodiments, $Ar_1$ and $Ar_2$ are phenyl or substituted phenyl groups. R is preferably hydrogen or phenyl.

In one primary embodiment of this invention, A is a radical deriving from an alcohol or a carboxylic acid, i.e., the group which results when an alcohol or a carboxylic acid is reacted with the dibenzoylresorcinol compound. The examples which follow provide an illustration of some of the possible alcohols and carboxylic acids which could be used according to this invention. However, it appears that almost any alcohol or carboxylic acid would be suitable.

For example, the alcohol could be a linear or branched aliphatic group, usually containing from 1 to about 20 carbon atoms. As a non-limiting illustration, the aliphatic portion of the alcohol could be methyl, ethyl, propyl, isopropyl, butyl, isobutyl, sec-butyl, tert-butyl, amyl, isoamyl, hexyl, octyl, decyl, dodecyl, and the like. Included within the definition of "alcohol" herein are the many derivatives, e.g., alcohols containing substituents such as halogens, or those containing carbocyclic or heterocyclic rings attached to the main aliphatic chain, or to a branch which itself is attached to the main chain.

The alcohol itself could alternatively be carbocyclic or heterocyclic, and can contain at least one aliphatic branch or aromatic ring which comprises from 1 to about 20 carbon atoms. Examples of carbocyclic alcohols are cyclohexanol, cyclopentanol, cyclooctanol, cyclodecanol, cyclododecanol, exo-norborneol, and derivatives of any of the foregoing which contain at least one aliphatic branch or aromatic carbon ring. These types of compounds are available commercially, or can usually be made by those skilled in the art, without undue effort.

Heterocyclic alcohols (containing one or more ring-structures) are also readily available. Most often, these alcohols include at least one nitrogen atom, sulfur atom, or oxygen atom in at least one of the cyclic chains. An example of a heterocyclic alcohol is piperidinol. Substituted piperidinols are also suitable, e.g., alkylated derivatives. One piperidinol-based compound of particular interest is 2,2,6,6-tetramethyl piperidinol, which functions as a hindered amine light stabilizer ("HALS") for plastics. Thus, the chemical attachment of a HALS group to a dibenzoykesorcinol compound is within the scope of the present invention.

The alcohol from which group A is derived could also be a diol, a derivative of a diol, a polymerized diol, or a derivative of a polymerized diol. All of these types of materials are also well-known in the art. As but one example, the diol could be alkane-based, e.g., one containing from about 2 to about 20 carbon atoms, such as propanediol, butanediol, pentanediol, and hexanediol. (This invention embraces all known versions of such compounds. For example, "propanediol" is meant to include 1,2-propane diol or 1,3-propane diol, alternatively known as 1,2-propylene glycol and trimethylene glycol, respectively). Various other glycols could be used, such as ethylene glycol or neopentyl glycol. Moreover, exemplary polymerized diols include polyethylene glycol and polypropylene glycol.

Those of ordinary skill in the polymer arts are familiar with derivatives of diols or polymerized diols which could be suitable for the present invention, based on the teachings herein. For example, one of the hydroxyl sites on the diols could be esterified by dehydration or catalytic agents to form the corresponding ester. Selection of a particular derivative will be determined in large part by the desired requirements for the compound being prepared, as well as the requirements for the end use-situation in which the compound is being utilized, e.g., as a coating composition for a particular thermoplastic.

The alcohol could alternatively be a polyol, i.e., a compound containing three or more hydroxyl groups. Examples of suitable polyols are glycerol, pentaerythritol, or dipentaerythritol. Moreover, in some embodiments, the polyol could be partially esterified, e.g., an ester could be formed at at least one of the hydroxyl sites, while a remaining, free hydroxyl group forms an ether linkage with the dibenzoylresorcinol moiety. The ester or another free hydroxyl group could in turn undergo further reaction for additional functionalization, e.g., reaction with vinyl chloride or with an acrylic or methacrylic group for the purpose of adding vinyl-type functionality.

In general, polyfunctional alcohols represent yet another class from which group A could be derived. The polyols could fall into this class. As an illustration, a material like the above-mentioned dipentaerythritol contains six primary hydroxyl groups which are functional sites, e.g., which are each esterifiable. Other polyfunctional alcohols could include at least one carboxylic acid group in addition to a hydroxyl group. Those skilled in organic synthesis are familiar with techniques for selectively reacting individual functional sites to obtain a particular organic product.

As mentioned previously, there is no restriction on the type of carboxylic acid which could be used to form group A of formula I. Usually, the acid belongs to one of the following classes: polycarboxylic acids, branched derivatives of mono- or polycarboxylic acids; cyclic derivatives of mono- or polycarboxylic acids, and functional derivatives of mono- or polycarboxylic acids. Some related compounds are described in the referenced, U.S. Pat. No. 5,763,674 of James E. Pickett et al.

Non-limiting examples of suitable polycarboxylic acids from which group A could be derived are succinic acid, glutaric acid, adipic acid, suberic acid, palmitic acid, azelaic acid, malonic acid, oxalic acid, maleic acid, fumaric acid, and phthalic acid. Many ester derivatives of these acids could also be employed. In other words, one or more of the carboxylic groups could be esterified, while a remaining, free carboxylic group forms an ester linkage with the dibenzoylresorcinol moiety.

Moreover, the carboxylic acid could contain various other types of chemical groups. For example, the acid could include at least one polyether linkage within a carbon atom chain. Furthermore, the polyether linkage could itself be readily substituted with various pendent chains, cyclic groups, or heterocyclic groups. Depending on various factors, such as the desired solubility for the final product-compound, one or more of the pendent chains could be acid-functionalized. Hydroxyl groups could also be incorporated into the polymer chains.

Other functional derivatives of the mono- and polycarboxylic acids could be prepared by the inclusion of at least one vinyl group or allyl group. As mentioned earlier, techniques for this type of functionalization are well-known in the art. In some preferred embodiments, the derivative is formed by the incorporation of at least one acrylic group or methacrylic group, as shown in the examples which follow. In general, the use of the vinyl group or allyl group permits a very effective reaction of the resulting compound with a copolymerizable monomer. Examples of the suitable copolymerizable monomers are acrylates, methacrylates, styrenes, and substituted derivatives of any of the foregoing materials. These types of reactions would result in the formation of very useful copolymers. For example, the copolymerizable monomers could constitute a portion of a matrix composition (as discussed below) for a UV-absorbing coating. Thus, copolymer linkages would be established between the matrix and the dibenzoylresorcinol compound.

Another aspect of the present invention is directed to methods for preparing compounds of formula I. When A is a radical deriving from an alcohol or a carboxylic acid, the compound is usually prepared by a process which comprises:

(a) reacting a mixture of a 4,6-dibenzoylresorcinol and a para-aldehyde with a secondary amine catalyst and a carboxylic acid solvent under reactive conditions to form a methylene carboxylate intermediate in which the methylene bridge forms a linkage between the dibenzoylresorcinol residue and a carboxylate moiety; and then (b) reacting the methylene carboxylate compound formed in step (a) with an alcohol or a carboxylic acid in a reactive medium to form the derivative.

Suitable processes for carrying out step (a), i.e., formation of the intermediate, are described in U.S. Pat. No. 5,763,674 mentioned above. A similar process (which may be thought of as a variation of the Mannich reaction) is also described in JP 79/19,950 (CA 91: 20116z). Thus, the present teachings do not need to be exhaustive in regard to this step. Briefly, examples of para-aldehydes suitable for the first step of the reaction are paraformaldehyde and paracetaldehyde (paraldehyde), with paraformaldehyde usually being the material of choice. Any secondary amine appears to be suitable for catalysis, such as diethylamine, dipropylamine, dibutylamine, dihexylamine, and dioctylamine. Various carboxylic acid solvents could be used, with acetic acid usually being selected, based in part on cost considerations.

The JP 79/19950 reference mentioned above calls for the use of relatively high levels of amine catalyst—about 40 mole %. However, it has recently been discovered that lower levels of catalyst reduce the amount of undesirable diethylamine-substituted derivatives. Thus, in the present invention, the amount of secondary amine catalyst employed in step (a) should usually be less than about 20 mole %, based on the molar weight of the 4,6-dibenzoylresorcinol. In preferred embodiments, the amount of secondary amine catalyst is less than about 10 mole %.

Some of the specific process details for carrying out step (a) and ensuring suitable "reaction conditions" would be familiar to those of ordinary skill in the art. In a typical embodiment, the reaction is carried out at a temperature of at least about 80° C. Following reaction, the mixture can be filtered, and the filtrate may then be diluted with additional carboxylic acid solvent. The filtrate could then be cooled, and the methylene acetate intermediate could be recovered in solid form by conventional separation techniques.

Step (b) of the process involves the reaction of the methylene acetate intermediate with an alcohol or a carboxylic acid, such as those described in detail previously. Many of the specific details regarding this step are provided in the examples which follow. Generally, the reactive medium is acidic, or at least neutral. This stage of the reaction is usually carried out at temperature in the range of about 20° C. to bout 120° C. Recovery of the product can be accomplished by conventional procedures.

It should be apparent from this discussion that step (b) results in the formation of an ether or ester link (depending on the use of either an alcohol or carboxylic acid, respectively) between the methylene carboxylate intermediate of the dibenzoylresorcinol molecule and the "A" group. In the case of using an alcohol, this result is somewhat surprising to those skilled in organic synthesis, since one might have expected the primary reaction to have involved displacement at the carbonyl site of the carboxylate intermediate, to form a less desirable product by transesterification.

Thus, in one respect, the reaction to form the compound of structure I, when A is a radical deriving from an alcohol, can be viewed as an etherification reaction which involves the combination of a compound of structure

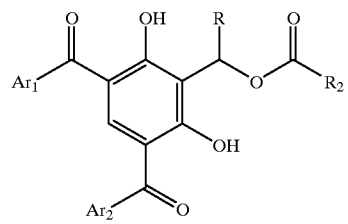

II with an alcohol in a suitable reaction medium, wherein R, $Ar_1$ and $Ar_2$ are as described above, and $R_2$ is a linear or branched alkyl chain containing less than about 10 carbon atoms. The $R_2$ moiety is usually introduced as part of the reaction medium. For example, if acetic acid is employed, then $R_2$ would be a methyl group; and if propionic acid is used, then $R_2$ would be an ethyl group. Other conventional details regarding the reaction medium are described in this specification, and would also be apparent to those of ordinary skill in the art.

As set forth above, another class of compounds from which the "A" group of formula I could be derived are substituted or unsubstituted aryl groups which do not include a pendent hydroxyl group. Suitable examples of this class are phenyl, alkyl-substituted phenyl groups, halogen-substituted phenyl groups, and alkoxy-substituted phenyl groups. These general types of groups are themselves known in the art, as are substituted versions, e.g., groups having pendent alkyl chains, pendent aromatic rings, pendent carbocyclic rings, and/or pendent heterocyclic rings.

Of particular interest for some embodiments of the present invention are aryl compounds in which a vinyl group is attached thereto (e.g., styryl derivatives). The vinyl group is usually attached to the 3-position or the 4-position on the aryl ring, relative to the attachment site of group A of formula I. Mixtures of isomers of such groups in both the 3- and 4-positions are also within the scope of the present invention. The vinyl-functionality permits the preparation of various, useful copolymer products, such as co-polymerizable UV absorbers.

In brief, the compounds in which the "A" group is derived from a substituted or unsubstituted aryl group can be prepared by a process (usually one-step) which comprises reacting a 4,6-dibenzoylresorcinol with a benzyl halide compound, an aqueous base, and a compatible phase transfer catalyst under conditions suitable for obtaining a substantial yield of the compound. The reaction is usually carried out at a temperature in the range of about 40° C. to about 120° C. Many different benzyl halide compounds could be used, depending on the desired product-structure. Non-limiting examples are benzyl bromide, benzyl chloride, 3-vinyl benzyl chloride, 3-vinyl benzyl bromide, 4-vinyl benzyl chloride, and 4-vinyl benzyl bromide.

There also appears to be no restriction on the type of base used. Examples are sodium hydroxide, potassium hydroxide, sodium carbonate, potassium carbonate, lithium hydroxide, and lithium carbonate. Moreover, a wide variety of phase transfer catalysts could be employed, such as tetrabutylammonium bromide, tetrabutylammonium chloride, benzyl trimethylammonium chloride, benzyl trimethylammonium bromide, tetraethylammonium bromide, and tetraethylammonium chloride. Those of ordinary skill in the art will be able to select the most appropriate starting materials and quantities of materials to obtain a substantial yield of a desired compound-product, based on the teachings herein, as well as a general knowledge of organic synthesis. The product can be recovered by conventional techniques.

Yet another aspect of the present invention is directed to a novel coating composition based in part on the dibenzoylresorcinol compounds described above. In general, these coating compositions exhibit a relatively high degree of photostability, and are capable of absorbing ultraviolet light. The compositions include a polymer matrix (usually transparent) which is compatible with the dibenzoylresorcinol compounds, e.g., in which there is very little phase separation when the components are mixed together. A wide variety of matrices may be used, such as polymer materials based on urethanes, melamines, acrylics, and methacrylics, as well as polycarbonates, polystyrenes, and the like. Various mixtures of any of these materials may also be employed, as well as copolymers. Poly(methyl methacrylate) is the preferred matrix material in some embodiments. The coating compositions usually comprise at least about 1% by weight of the dibenzoylresorcinol-based compounds described above, based on the total weight of the coating. In many preferred embodiments, the coating compositions comprise at least about 10% by weight of the dibenzoylresorcinol-based compounds, while in some especially preferred embodiments, the level is at least about 35% by weight. The most appropriate level will of course depend on various factors, such as the particular compound being used, the particular substrate being treated, and the degree of UV protection required for a particular end use.

Many of the materials (such as the acrylic polymers) may be used in conjunction with organic solvents. Moreover, aqueous emulsions of some of the materials may be utilized, e.g., acrylic emulsions in which the dibenzoylresorcinol-based compounds are dispersed. Techniques for preparing these types of coating compositions are well-known in the art, and are described in many references, such as U.S. Pat. Nos. 5,391,795; 4,373,061; 4,322,455; and 4,278,804, each of which is incorporated herein by reference. The compositions may contain various other components and additives in effective amounts, such as catalysts, photoinitiators, surfactants, dispersants, stabilizers, anti-settling agents, abrasion resistance agents (e.g., silica); and additional UV absorbers.

A further aspect of the present invention relates to solid substrates on which coating compositions like those described above are applied. There is generally no limitation with respect to the type of substrate which may be coated. Examples include polymer substrates such as those based on acrylics (e.g., poly(methyl methacrylate); polyesters such as poly(ethylene terephthalate) and poly(butylene terephthalate); polyamides, polyimides, acrylonitrile-styrene copolymers; styrene-acrylonitrile-butadiene copolymers; polyvinyl chloride, polystyrene, blends of polystyrene and polyphenylene ether; butyrates, polyethylene, and the like, as well as various copolymers which include any of the above-listed materials. Moreover, the coating compositions may be applied to other types of substrates, e.g., metal substrates, painted surfaces, glass, ceramics, and textiles.

Thermoplastic substrates are frequently provided with protective coatings. Within that class, polycarbonates and copolymers such as polyesterpolycarbonates are often the substrates which receive the most benefit from the coating compositions of the present invention. These types of polymers are well-known in the art and described in numerous patents and other references, such as *Organic Polymer Chemistry*, by K. J. Saunders, 1973, Chapman and Hall Ltd. The polycarbonates are usually prepared from aromatic dihydroxy compounds such as bisphenol A, using well-known techniques, such as interfacial polymerization or melt polymerization.

Methods for applying the protective coatings to the substrate are also known in the art, and described in many of the references set forth above. Usually, a relatively thin layer of the matrix material is applied to the substrate by various techniques, such as spraying, dipping, flow-coating, roll-coating, and the like. After the coating has been applied to the substrate, substantially all of the volatile components (e.g., water or organic solvents) are evaporated—usually, by air-drying or heating. A relatively uniform polymer layer containing the dibenzoylresorcinol-based compound remains. Additional heating steps may be used to remove any residual solvents. The thickness of this coating layer after removal of the volatile components is usually in the range of about 0.01 micron to about 50 microns, and preferably, from about 0.1 micron to about 10 microns.

Coatings based on thermosetting polymers or emulsions usually require baking at elevated temperature to effect curing. Those of ordinary skill in the art are familiar with procedures for curing other types of coating systems also, e.g., radiation-curable coatings such as those described in U.S. patent application Ser. No. 08/699,254, filed on Aug. 15, 1996 now U.S. Pat. No. 5,990,188.

EXAMPLES

All of these examples are merely illustrative, and should not be construed to be any sort of limitation on the scope of the claimed invention.

Examples 1–6 are best understood by reference to Exemplary Reaction Scheme 1, based on the present invention. $Et_2NH$ is diethylamine; $(CH_2O)_n$ is paraformaldehyde; "HOAc" represents acetic acid; and ROH designates an alcohol, as explained below.

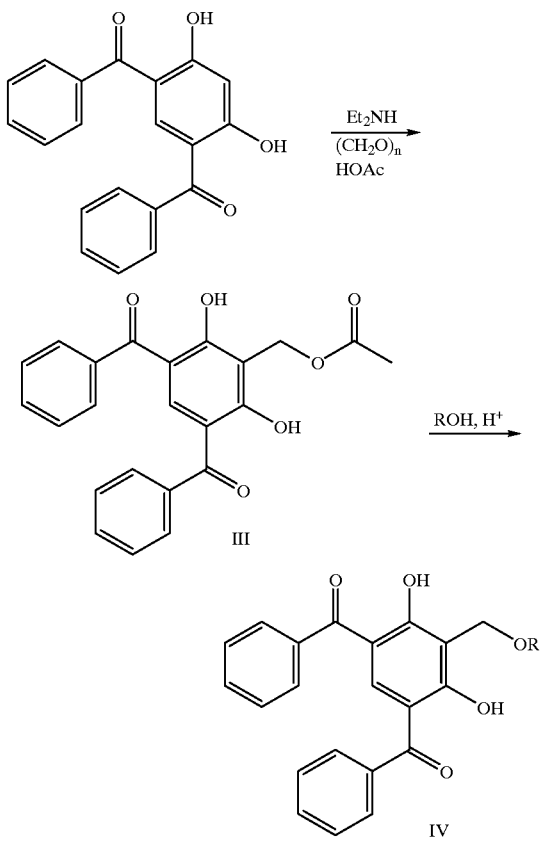

Example 1

The preparation of 2-(acetoxymethyl)-4,6-dibenzoylresorcinol (III) was carried out in this example. 4,6-Dibenzoylresorcinol (63.6 g, 200 mmol), paraformaldehyde (9 g, 300 mmol), and diethylamine (1.0 mL, 10 mmol) were combined in about 65 mL of glacial acetic acid. The mixture was stirred and heated at 100° C. for 16 hours. The mixture was filtered while hot. The filtrate was diluted with an additional 40 mL of acetic acid, cooled, and filtered to yield the acetate III: 52.0 g, 68% yield. NMR (300 MHz, CDCl$_3$): 2.15 ppm (s, 3H); 5.40 ppm (s, 2H), 7.4–7.6 ppm (m, 10H); 8.08 ppm (s, 1H); 13.45 ppm (s, 2H).

Example 2

The preparation of 2-(ethoxymethyl)-4,6-dibenzoylresorcinol (IV, R=ethyl) is carried out in this example. Acetate III (11.7 g, 30 mmol) and 0.5 mL of concentrated hydrochloric acid were added to about 30 mL of ethanol. The mixture was stirred and heated at reflux overnight and then cooled. The solid product was filtered, washed with ethanol, and dried to give the product: 9.15 g, 81% yield. NMR (300 MHz, CDCl$_3$): 1.28 ppm (t, 3H); 3.70 ppm (q, 2H); 4.75 ppm (s, 2H); 7.4–7.6 ppm (m, 10H); 8.00 ppm (s, 1H); 13.35 ppm (s, 2H).

Example 3

This example describes the preparation of 2-(isopropoxymethyl)-4,6-dibenzoylresorcinol (IV, R=isopropyl). Acetate III (3.90 g, 10 mmol) and 2 drops of concentrated hydrochloric acid were added to about 15 mL of isopropyl alcohol. The mixture was stirred and heated at reflux overnight and then cooled. The solid product was filtered, washed with isopropyl alcohol, and dried to give the product: 3.34 g, 86% yield. NMR (300 MHz, CDCl$_3$): 1.30 ppm (d, 6H); 3.85 ppm (heptet, 1H); 4.75 ppm (s, 2H); 7.4–7.6 ppm (m, 10H); 8.00 ppm (s, 1H); 13.30 ppm (s, 2H).

Example 4

In this example, 2-(t-butoxymethyl)-4,6-dibenzoylresorcinol (IV, R=tertiary-butyl) is prepared. Acetate III (3.90 g, 10 mmol) and 5 drops of concentrated hydrochloric acid were added to about 15 mL of tert-butyl alcohol. The mixture was stirred and heated at reflux overnight and then cooled. The solid product was filtered, washed with isopropyl alcohol, and dried to give the product: 3.62 g, 90% yield. NMR (300 MHz, CDCl$_3$): 1.37 ppm (s, 9H); 4.67 ppm (s, 2H); 7.4–7.6 ppm (m, 10H); 7.94 ppm (s, 1H); 13.23 ppm (s, 2H).

Example 5

The preparation of 2-(2-methacryloxyethoxymethyl)-4,6-dibenzoylresorcinol (IV, R=CH$_2$CH$_2$OCOC(CH$_2$)=CH$_2$) was carried out. Acetate III (9.75 g, 25 mmol) and 2-hydroxyethylmethacrylate (6.5 g, 50 mmol) were combined with 100 mg of p-toluenesulfonic acid monohydrate and 10 mL of toluene. The mixture was brought to reflux and heated for about 1.25 hours, after which it was cooled and diluted with 100 mL of ethanol. The volume was reduced by about half, and a small amount of gummy material was removed. After stirring at room temperature overnight, the resulting solid was filtered and taken up in warm methylene chloride/isopropyl alcohol. As the mixture cooled, a gummy solid formed. The solution was decanted from the solid and allowed to cool to room temperature. The resulting solid was filtered and washed with isopropyl alcohol to give the product: 2.35 g, 20% yield. NMR (300 MHz, CDCl$_3$): 1.98 ppm (s, 3H); 3.90 ppm (t, 2H); 4.40 ppm (t, 2H); 4.82 ppm (s, 2H); 5.59 ppm (bs, 1H); 6.19 ppm (bs, 1H); 7.4–7.6 ppm (m, 10H); 8.02 ppm (s, 1H); 13.40 ppm (s, 2H).

Example 6

This example describes the preparation of 4,6-dibenzoyl-2-(8-hydroxy-2-oxa-octyl)resorcinol (IV, R=(CH$_2$)$_6$OH). Acetate III (1.0 g, 2.5 mmol) and 5 g of 1,6-hexanediol (42 mmol) were heated at 1350° C. overnight. The reaction mixture was then cooled, taken up in 2-propanol, and filtered. Water was added to the filtrate to precipitate the product which was filtered and dried to yield 0.75 g (67%) of white solid. The NMR spectrum was consistent with the assigned structure.

Examples 7–9 relate to Exemplary Reaction Scheme 2, wherein "R'COOH" is a carboxylic acid, as indicated in the examples:

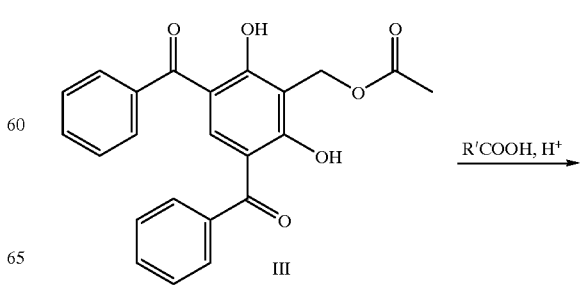

-continued

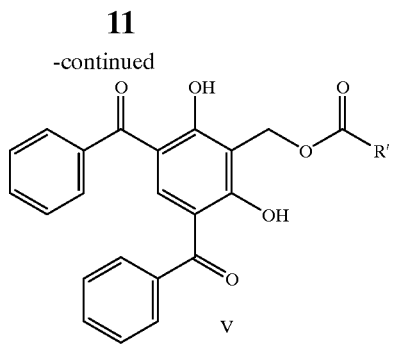

V

Example 7

The preparation of mixed 4,6-dibenzoyl-2-(acryloxymethyl)resorcinol (VI structure V where R'=CH=CH$_2$) was carried out in this example. The preparation of 4,6-dibenzoyl-2-(2-acryloxypropoxymethyl) resorcinol (VII, structure V, where R'=CH$_2$CH$_2$OC(O)CH=CH$_2$) was also carried out. Acetate III (3.9 g, 10 mmol) was added to 20 g of acrylic acid, and the mixture was heated at 105–110° C. for 3 hours. The reaction mixture was then cooled, and the product precipitated upon addition of 2-propanol and water. It was filtered and dried to yield 4.07 g of a product consisting of about ⅔ of structure VI and ⅓ of structure VII as revealed by NMR spectroscopy.

Example 8

In this example, the preparation of 4,6-dibenzoyl-2-(methacryloxymethyl)resorcinol (V, where R'=C(CH$_3$)=CH$_2$) is described. Acetate III (3.9 g, 10 mmol) was added to 22 g of methacrylic acid and the mixture was heated at about 135° C. for 18 hours. The reaction mixture was then cooled, and the product precipitated upon addition of 2-propanol and water. It was filtered and dried to yield 3.85 g of a product with an NMR spectrum consistent with the assigned structure.

Example 9

In this experiment, UV-curable coating formulations within the scope of the present invention were prepared and tested. Table 1 describes the components which were combined by conventional techniques in the preparation:

TABLE 1

Coating compositions (parts by weight)

| Component | A | B | C | D |
|---|---|---|---|---|
| Polyurethane hexacrylate (Ebecryl ® 1260) | 8 | 8 | 8 | 8 |
| FCS100 (GE Silicones acrylated colloidal silica) | 2 | 2 | 2 | 2 |
| Tinuvin ® 123 (Ciba Geigy) | 0.1 | 0.1 | 0.1 | 0.1 |
| Surfactant | 0.015 | 0.015 | 0.015 | 0.015 |
| 2,4,6-trimethylbenzoyl diphenyl phosphine oxide (initiator) | 0.3 | 0.3 | 0.3 | 0.3 |
| Isopropyl alcohol/propylene glycol monomethyl ether (1:1) | 20 | 20 | 20 | 20 |
| 2-(acetoxymethyl)-4,6-dibenzoylresorcinol | 0.5 | — | — | — |
| 4,6-dibenzoyl-2-(8-hydroxy-2-oxa-octyl)resorcinol | — | 0.5 | — | — |
| 4,6-dibenzoyl-2-(acryloxymethyl)resorcinol | — | — | 0.5 | — |
| 4,6-dibenzoyl-2-(methacryloxymethyl)resorcinol | — | — | — | 0.5 |

The formulations were stirred in the dark for three days and then flow-coated onto pre-cleaned Lexan® polycarbonate panels. The resulting coatings were air dried for one minute, dried at 70° C. for four minutes, and then exposed to UV light by passing them five times under two 300 watt/inch medium pressure mercury lamps, using a conveyor moving at 25 ft/min.

The coated panels were then exposed in an Atlas Ci35a xenon arc Weathero-meter® equipped with borosilicate inner and outer filters, operating at 0.77 W/m$^2$ irradiance at 340 run in a cycle of 160 minutes light, 5 minutes dark, 15 minutes dark with water spray. This cycle applies 2.46 kJ/m$^2$ of energy at 340 nm per hour of operation. Table 2 shows the change in Yellowness Index (ASTM D-1925) after 585 hours of weathering. It can be seen from Table 2 that in every case the UV absorber improved the yellowing performance relative to the uncoated control sample.

TABLE 2

Weathering of coated polycarbonate panels

| Formulation (Table 1) | Delta YI - Weathering (after 585 hr) |
|---|---|
| Uncoated Control | 8.6 |
| A | 0.3 |
| B | 0.5 |
| C | 0.7 |
| D | 2.1 |

Examples 10 and 11 describe the preparation of additional compounds according to Exemplary Reaction Schemes 1 and 2.

Example 10

The preparation of ester VIII (structure V, R'=CH$_2$OCH$_2$CH$_2$OCH$_2$-CH$_2$OCH$_3$) was carried out. Acetate III (3.9 g, 10 mmol) and 2-[2-(2-methoxyethoxy) ethoxy]acetic acid (1.78 g, 10 mmol) were combined in about 15 mL of toluene and heated at reflux for 5 hours. The toluene was then distilled from the reaction mixture, replaced with fresh toluene, distilled, replaced with fresh toluene again, and distilled once more. The reaction mixture was then cooled, taken up in ether, and filtered to yield 4.13 g (81%) of compound VIII.

Example 11

The preparation of ester IX and X (structure V, R'=(CH$_2$)$_6$COOH and the diester) is described in this example. Acetate III (3.9 g, 10 mmol) and suberic acid (17.4 g, 100 mmol) were combined in 15 mL of toluene and heated at reflux overnight. The toluene was distilled and replaced with fresh toluene. This step was repeated 2 more times. The reaction mixture was diluted with 25 mL of toluene and cooled, whereupon the excess suberic acid crystallized and was filtered and recovered (11.8 g, 9 mmol). The filtrate was evaporated, taken up in ether, and filtered to yield 3.94 g of product. NMR analysis revealed that the product consisted of a mixture of approximately 3 parts of compound IX to 2 parts of compound X, the diester derivative of suberic acid:

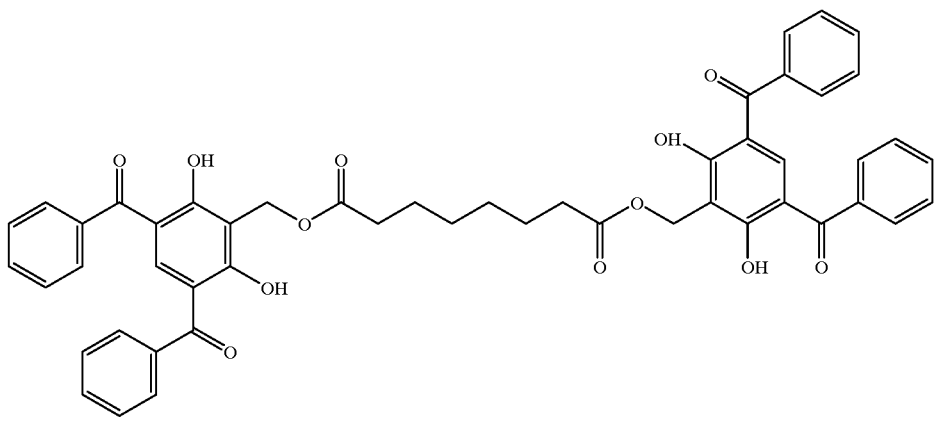

Compound X

Example 12

This example describes the preparation of 2-(2,2,6,6-tetramethyl piperidinol)-4,6-dibenzoylresorcinol, a "DBR-HALS" dibenzoylresorcinol-hindered amine light stabilizer) which is useful as a UV absorber for various substrates, such as those based on acrylate or methacrylate polymers. The compound prepared had the following structure:

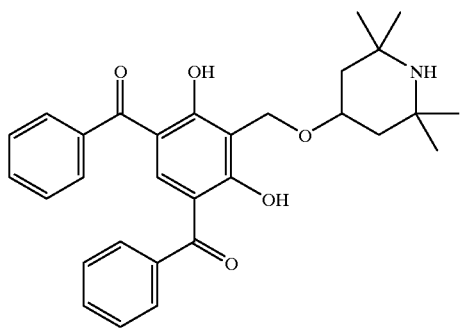

(DBR-HALS DERIVATIVE COMPOUND)

In preparing this compound, 2.6 mmol (1 g) of 2-(methylacetoxyl)-4,6-dibenzoylresorcinol and 2.6 (0.4 g) of 2,2,6,6-tetramethyl-4-piperidinol were dissolved in a xylene-based solvent, and brought to reflux at 140° C. The reaction proceeded for about 16 hours. The reaction mixture was then precipitated, filtered, and washed with isopropanol. The product was then dried in a vacuum oven at 50° C. overnight. Analytical characterization (FD-MS) showed a parent ion with m/z 488, as calculated for the structure set forth above.

Films were then prepared for xenon arc accelerated testing. A 5.33 g portion of a polymethylmethacrylate (PMMA) polymer, Elvacite ™2041, was dissolved to completion in 80.5 g of 2-methoxypropanol and 14.2 g of diacetone alcohol at 50° C. in a three-neck flask equipped with a mechanical stirrer and heating mantle. A 25 g aliquot of the polymer solution and 0.07 g of UV absorber were combined to make a 5 wt. % solids solution of UV absorber in polymer solution. The prepared solutions were rotated on a roll mill overnight, to allow the UV absorber to dissolve.

The solutions were then flow-coated onto unstabilized films of Lexan® polymer having a thickness of 15 mils. The flow coating was carried out at 22° C. and 50% relative humidity. A 15 minute solvent flash was allowed before the films were mounted and exposed to a 105° C. oven for 30 minutes.

The xenon arc accelerated testing was performed on a Ci35a xenon arc Weather-ometer®, using type S borosilicate inner and outer filters. The irradiance level was 0.77 W/m² at 340 nm. The black panel temperature was between 70–73° C.; and the dry bulb temperature was 45° C., with a wet bulb depression of 10° C. (50% relative humidity). The cycle was 160 min. light, 5 minutes dark, 15 minutes dark, with water spray. This cycle accumulates 2.46 KJ/m² at 340 nm per hour of operation.

The color, haze, and transmittance measurements were taken using a Gardner XL-835 colorimeter. These measurements are reported as CIELAB L*, a*, b* and YI D, spectral component excluded. The exposure time was 495.7 operational hours.

TABLE 3

| Sample | Final Delta (YI) |
|---|---|
| DBR-HALS | 3.4 |
| Control* | 8.9 |

*(PMMA-coated Lexan ® sheet)

The following examples relate to the reaction of 4,6-dibenzoylresorcinol with benzyl halides to produce materials based on another embodiment of this invention. The reactions generally follow Exemplary Reaction Scheme 3, wherein the components are described in the examples:

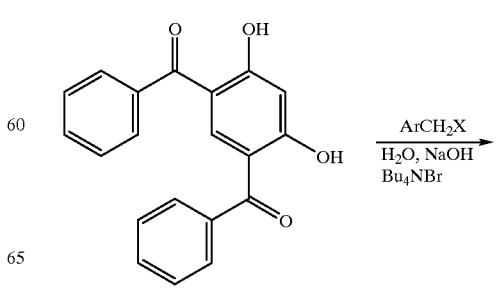

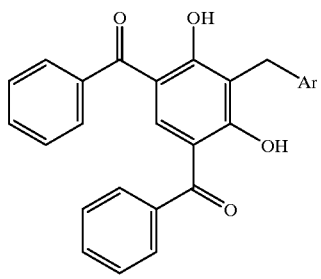

Example 13

In this example, 2-benzyl4,6-dibenzoylresorcinol (XI) was prepared. 4,6-Dibenzoylresorcinol (3.18 g, 10 mmol), benzyl chloride (1.25 mL, 11 mmol), and tetrabutylammonium bromide (about 20 mg) were added to a solution of sodium hydroxide (0.80 g, 20 mmol) in 10 mL of water. The reaction mixture was stirred and warmed to about 40° C. for approximately 2–3 hours, and then stirred at room temperature overnight. To the reaction mixture was added about 15 mL of 5% aqueous HCl. The reaction mixture was extracted into methylene chloride, evaporated to dryness, and recrystallized from chloroform/ethanol to afford 2-benzyl-4,6-dibenzoylresorcinol (2.67 g, 65% yield) in two crops. $^1$H NMR (300 MHz, CDCl$_3$): 4.16 (s, 2H); 7.2–7.6 (m, 15H); 7.91 (s, 1H); 13.29 (s, 2H). NMR analysis of the reaction mixture disclosed that a small amount of the O-benzyl derivative had formed as well.

Example 14

This example describes the preparation of 2-(3 and 4-vinylbenzyl)-4,6-dibenzoylresorcinol (XII): 4,6-Dibenzoylresorcinol (31.8 g, 100 mmol), mixed 3 and 4-chloromethylstyrene (15.4 g, 100 mmol), and tetrabutylammonium bromide (0.32 g) were added to a solution of sodium hydroxide (4.4 g, 110 mmol) in 100 mL of water. The reaction mixture was stirred and heated to 60° C. After 1 hour a precipitate formed, and 30 mL of toluene was added to make a two-phase solution. The mixture was heated and stirred for 48 hours after which it was cooled. The aqueous phase was decanted from the solidified organic phase. About 100 mL of ethanol was added, and the resulting slurry was filtered and washed with ethanol. Recrystallization from ethanol/chloroform afforded the product as a white powder (27.0 g, 62% yield). NMR analysis was consistent with the product being about 20% of the O-alkylated derivative and 80% of the C-alkylated derivative (XII).

Example 15

This example is similar to those of examples 13 and 14, with the replacement of ArCH$_2$X with ArCHRX (wherein X is a halide), according to Exemplary Reaction Scheme 3, shown above. 4,6-dibenzoyl-2-(1-phenylethyl)resorcinol (XIII, structure I with R=methyl; and Ar$_1$, Ar$_2$, and A=phenyl) was prepared as follows. 4,6-Dibenzoylresorcinol (3.18 g, 10 mmol), 1-bromoethylbenzene (2.04 g, 11 mmol) and about 30 mg of tetrabutylammonium bromide were added to a solution of 0.8 g (20 mmol) of sodium hydroxide in 10 mL of water. The temperature was brought to about 80° C. and stirred vigorously for 2 hours whereupon 1 g more of the 1-bromoethylbenzene was added, and heating and stirring was continued for another 2 hours. The reaction mixture was then cooled, acidified with concentrated hydrochloric acid, and extracted into chloroform. The organic layer was separated, dried, and evaporated to give a solid that was twice recrystallized from ethanol/chloroform to yield 1.91 g (45.5%) of solid in two crops. The NMR spectrum was consistent with the assigned structure.

Example 16

This example is similar to example 15, and involved the preparation of 4,6-dibenzoyl-2-(diphenylmethyl)resorcinol (XIV, structure I with Ar$_1$, Ar$_2$, A, and R=phenyl). 4,6-Dibenzoylresorcinol (3.18 g, 10 mmol), chlorodiphenylmethane (2.22 g, 11 mmol) and about 30 mg of tetrabutylammonium bromide were added to a solution of 0.8 g (20 mmol) of sodium hydroxide in 10 mL of water. The temperature was brought to about 80° C. and stirred vigorously for 2 hours whereupon 1 g more of the chlorodiphenylmethane was added. Heating and stirring were continued for another 2 hours. The reaction mixture was then cooled, acidified with concentrated hydrochloric acid, and extracted into chloroform. The organic layer was separated, dried, and evaporated to give a solid that was twice recrystallized from ethanol/chloroform to yield 0.62 g (13%) of solid in two crops. The NMR spectrum was consistent with the assigned structure.

Example 17

UV-curable coating formulations were prepared in a conventional manner:

TABLE 4

| Coating compositions (parts by weight) | | | | |
|---|---|---|---|---|
| Component | A | B | C | D |
| Polyurethane hexacrylate Ebecryl ® 1260) | 8 | 8 | 8 | 8 |
| FCS100 (GE Silicones acrylated colloidal silica) | 2 | 2 | 2 | 2 |
| Tinuvin ® 123 (Ciba Geigy) | 0.1 | 0.1 | 0.1 | 0.1 |
| Surfactant | 0.015 | 0.015 | 0.015 | 0.015 |
| 2,4,6-trimethylbenzoyl diphenyl phosphine oxide (initiator) | 0.3 | 0.3 | 0.3 | 0.3 |
| Isopropyl alcohol/propylene glycol monomethyl ether (1:1) | 20 | 20 | 20 | 20 |
| 2-styrylmethyl-4,6-dibenzoylresorcinol (XII) | 0.5 | — | — | — |
| 2-benzyl-4,6-(dibenzoylresorcinol (XI) | — | 0.5 | — | — |
| 2-(1-phenylethyl)-4,6-dibenzoylresorcinol (XIII) | — | — | 0.5 | — |
| 4,6-dibenzoyl-2-(diphenylmethyl) resorcinol (XIV) | | | | 0.5 |

The formulations were stirred in the dark for three days and then flow coated onto pre-cleaned Lexan® polycarbonate panels. The resulting coatings were air dried for one minute, dried at 70° C. for four minutes, and then exposed to UV light by passing them five times under two 300 watt/inch medium pressure mercury lamps, using a conveyor moving at 25 ft/min.

The coated panels were then exposed in an Atlas Ci35a xenon arc Weathero-meter® equipped with borosilicate inner and outer filters, operating at 0.77 W/m$^2$ irradiance at 340 nm in a cycle of 160 minutes light, 5 minutes dark, 15 minutes dark with water spray. This cycle applies 2.46 kJ/m$^2$ of energy at 340 nm per hour of operation. Table 5 shows the change in Yellowness Index (ASTM D-1925) after 585 hours of weathering. It can be seen from Table 5 (below) that in every case, the UV absorber improved the yellowing performance relative to the uncoated control sample.

TABLE 5

Weathering of coated polycarbonate panels

| Formulation (Table 4) | Delta YI - after 585 hr weathering |
|---|---|
| uncoated control | 8.6 |
| A | 1.7 |
| B | 5.3 |
| C | 2.8 |
| D | 2.8 |

While preferred embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

All of the patents, patent applications, articles, and texts mentioned above are incorporated herein by reference.

What is claimed is:

1. A method for preparing a derivative of a dibenzoylresorcinol compound, comprising the following steps:
   (a) reacting a mixture of a 4,6-dibenzoylresorcinol and a para-aldehyde with a secondary amine catalyst and a carboxylic acid solvent under reactive conditions to form a methylene carboxylate intermediate in which the methylene bridge forms a linkage between the dibenzoylresorcinol residue and a carboxylate moiety; and then
   (b) reacting the methylene carboxylate compound formed in step (a) with an alcohol or a carboxylic acid in a reactive medium to form the derivative.

2. The method of claim 1, wherein the para-aldehyde is paraformaldehyde, and the secondary amine catalyst is selected from the group consisting of diethylamine, dipropyl amine, dibutylamine, dihexylamine, and dioctylamine.

3. The method of claim 1, wherein the amount of secondary amine catalyst present is less than about 20 mole %, based on the molar weight of the 4,6-dibenzoylresorcinol.

4. The method of claim 3, wherein the amount of secondary amine catalyst present is less than about 10 mole %.

5. The method of claim 1, wherein the alcohol employed in step (b) is selected from the group consisting of linear alcohols, branched alcohols, carbocyclic alcohols, heterocyclic alcohols, diols, derivatives of diols, polyols, and functional derivatives of any of the foregoing.

6. The method of claim 1, wherein the carboxylic acid employed in step (b) is selected from the group consisting of monocarboxylic acids, polycarboxylic acids, branched derivatives of mono- or polycarboxylic acids; cyclic derivatives of mono- or polycarboxylic acids, and functional derivatives of mono- or polycarboxylic acids.

7. A method for preparing a derivative of a dibenzoylresorcinol compound, comprising the following steps:
   (a) reacting a mixture of a 4,6-dibenzoylresorcinol and paraformaldehyde with diethylamine catalyst and acetic acid solvent under reactive conditions to form a methylene carboxylate intermediate in which the methylene bridge forms a linkage between the dibenzoylresorcinol residue and an acetate moiety; and then
   (b) reacting the methylene acetate compound formed in step (a) with an alcohol in a reactive medium to form the derivative, the alcohol being selected from the group consisting of ethanol, isopropanol, tertiary-butanol, 2- hydroxyethylmethacrylate, 1,6-hexanediol, and 2,2,6,6-tetramethyl-4-piperidinol.

8. A method for preparing a derivative of a dibenzoylresorcinol compound, comprising the following steps:
   (a) reacting a mixture of a 4,6-dibenzoylresorcinol and paraformaldehyde with diethylamine catalyst and acetic acid solvent under reactive conditions to form a methylene carboxylate intermediate in which the methylene bridge forms a linkage between the dibenzoylresorcinol residue and an acetate moiety; and then
   (b) reacting the methylene acetate compound formed in step (a) with a carboxylic acid in a reactive medium to form the derivative, the carboxylic acid being selected from the group consisting of acrylic acid, methacrylic acid, 2-[2-(methoxyethoxy)ethoxy]acetic acid, and suberic acid.

* * * * *